United States Patent [19]

Cartmell et al.

[11] Patent Number: 4,669,468

[45] Date of Patent: Jun. 2, 1987

[54] CAPACITIVELY COUPLED INDIFFERENT ELECTRODE

[75] Inventors: James V. Cartmell; Joseph F. DeRosa, both of Dayton, Ohio

[73] Assignee: American Hospital Supply Corporation, Evanston, Ill.

[21] Appl. No.: 245,775

[22] Filed: Mar. 20, 1981

Related U.S. Application Data

[63] Continuation of Ser. No. 48,952, Jun. 15, 1979, abandoned.

[51] Int. Cl.$^4$ ............................................. A61B 17/39
[52] U.S. Cl. .................................. 128/303.13; 128/798
[58] Field of Search ...................... 128/303.13, 303.14, 128/639–641, 644, 783, 798, 802

[56] References Cited

U.S. PATENT DOCUMENTS

| | | | |
|---|---|---|---|
| 3,085,577 | 4/1963 | Berman et al. | 128/641 |
| 3,500,823 | 3/1970 | Richardson et al. | 128/639 |
| 3,568,662 | 3/1971 | Everett et al. | 128/639 |
| 3,744,482 | 7/1973 | Kaufman et al. | 128/639 |
| 3,746,004 | 7/1973 | Jankelson | 128/798 |
| 3,848,600 | 11/1974 | Patrick et al. | 128/303.13 |
| 3,972,329 | 8/1976 | Kaufman | 128/641 |
| 4,004,578 | 1/1977 | Palmius | 128/640 |
| 4,066,078 | 1/1978 | Berg | 128/641 |
| 4,117,846 | 10/1978 | Williams | 128/303.13 |
| 4,137,909 | 2/1979 | Hix | 128/641 |
| 4,166,465 | 9/1979 | Esty et al. | 128/303.13 |
| 4,188,927 | 2/1980 | Harris | 128/303.14 |

OTHER PUBLICATIONS

Investigations & Studies on Electrosurgery, Pearce et al, Submitted by: Bio-Medical Engineering Center, Purdue University.

Primary Examiner—Lee S. Cohen
Attorney, Agent, or Firm—Killworth, Gottman, Hagan & Schaeff

[57] ABSTRACT

A capacitively coupled indifferent electrode for use in electrosurgical procedures is provided which is safe and reliable in use. The electrode includes a backing material, an electrically conductive metal foil adhered to one surface of the pad, a layer of dielectric material completely overlying the foil, and a layer of pressure-sensitive adhesive covering the dielectric layer. The electrode is placed on a patient's skin and may be connected to the return side of an electrosurgical generator through a cable which is connected through the backing material to the electrode.

14 Claims, 8 Drawing Figures

CAPACITIVELY COUPLED INDIFFERENT ELECTRODE

This is a continuation of application Ser. No. 048,952 filed June 15, 1979, now abandoned.

BACKGROUND OF THE INVENTION

The present invention relates to medical electrodes used as indifferent electrodes in electrosurgical procedures, and more particularly to a capacitively coupled electrode having improved convenience, safety, and performance.

In electrosurgical procedures, an electrosurgical generator generates high radio frequency electric current which is fed to an active electrode. The active electrode is used to cut tissue and coagulate blood vessels and is activated for relatively short times during such procedures. An indifferent, or patient, electrode is placed in contact with a patient to provide a return path for the high frequency current to the generator, which is in turn typically connected directly to ground or to an isolated ground unit.

The input current is applied to the tissue by means of the active electrode which is preferably of small cross-section so that high current densities may be obtained at the surgical site. These high current densities provide the required heating (up to 1,000° C. at the point of contact) needed for the operating procedure. However, it is essential that the indifferent electrode have contact over sufficient surface area of the patient to insure that the return current has a low density to avoid burning or scarring of the patient's tissue which is in contact with the indifferent electrode.

Prior art indifferent electrodes have either been of the direct electrical contact type or of the capacitively coupled type. Direct electrical contact type indifferent electrodes have either been designed to be attached directly to or placed underneath a patient and have been available in both dry (direct metal contact to skin) and conductive gel or adhesive (electrode coupled to skin through a conductive solution, gel, or polymer) forms. However, direct electrical contact type electrodes suffer from a variety of problems. For example, if a pre-gelled form is used, the gel may have dried out prior to use or may dry out during surgical use, there may be bacterial growth in the gel, and there are patient cleanup problems in removing the gel after surgery. Additionally, the gel may cause skin irritation in some patients.

If a dry form direct electrical contact type electrode is utilized, usually in the form of a large surface area metal plate or foil, other problems arise. These include the possibility of burns caused by preferential current flow due to patient perspiration or spilled fluids at the contact site, burns caused by the movement of the patient during surgery which breaks contact with a substantial portion of the metal surface, and electrical hazards to physicians and other operating room personnel if a protruding edge of the metal electrode is accidently touched or comes in contact with other metal surfaces in the operating room.

Moreover, all previous types of direct electrical contact type indifferent electrodes suffered from hot spots around their leading edges caused by a preference of radio frequency electrical current to leave a patient's body at those points. This uneven current distribution through the electrodes accentuates possible patient burning or scarring problems.

Capacitive coupled electrodes, on the other hand, have the potential of being much safer in use. These types of electrodes have a dielectric material sandwiched between the metal electrode and the patient's skin. In the past, these electrodes have been held in position on a patient's skin by elastic bands, strips of adhesive tape, or a peripheral adhesive area around the edges of the capacitor structure. However, these prior art methods of securing the electrode to the patient are unreliable. If a patient is moved or repositioned, air gaps or tenting causes portions of the dielectric material to pull away from a patient's skin, creating hot spots and possibly causing burning or scarring of tissue. Accordingly, the need still exists in the art for a convenient, safe, and reliable indifferent electrode for use in electrosurgical procedures.

SUMMARY OF THE INVENTION

In accordance with the present invention, a capacitively coupled electrode is provided having a metal or other electrically conductive foil mounted on a foam or other suitably flexible material. In one embodiment, electrical contact is achieved by means of a metal rivet piercing the metal foil and passing through to the opposite side of the foam pad where it is mated with a metal socket which is then crimped to grip and hold the rivet. The metal socket can then be snap fitted to an electrical cable means which is in turn connected to the return side of an electrosurgical current generator. In another embodiment, an electrical cable and plug may be preattached to the electrode.

The metal foil is completely covered by a layer of dielectric material such as polyethylene terephthalate, polyvinylidene chloride, polyethylene, or polysulfone. In a preferred embodiment, the dielectric material is coated on both sides by a pressure-sensitive adhesive. Alternatively, the adhesive may be applied in a separate step during fabrication. The adhesive serves to attach securely the dielectric material to the metal foil and, when a protective releasable cover sheet is removed, serves to attach securely the electrode to a patient's skin. In an alternative embodiment, a metallized dielectric material may be utilized which eliminates the need for an adhesive between the dielectric material and the metal foil.

In use, the protective releasable cover sheet is peeled away and the electrode assembly is placed on the patient adhesive side down. The adhesive prevents any gaps or voids from forming and assures continuous contact of the dielectric material over the entire surface area of the electrode providing uniform electrical coupling to the skin. The shape of the electrode assembly is not critical, and it may be fabricated in a variety of different shapes adapted to be adhered to different portions of a patient's body. Typically, the assembly will have a rectangular configuration.

Accordingly, it is an object of this invention to provide an improved indifferent electrode for use in electrosurgical procedures which is safer to operate and more reliable than prior art electrodes. This and other objects and advantages of the invention will become apparent from the following description, the accompanying drawings, and the appended claims.

DESCRIPTION OF THE PREFERRED EMBODIMENT

Figure 1:
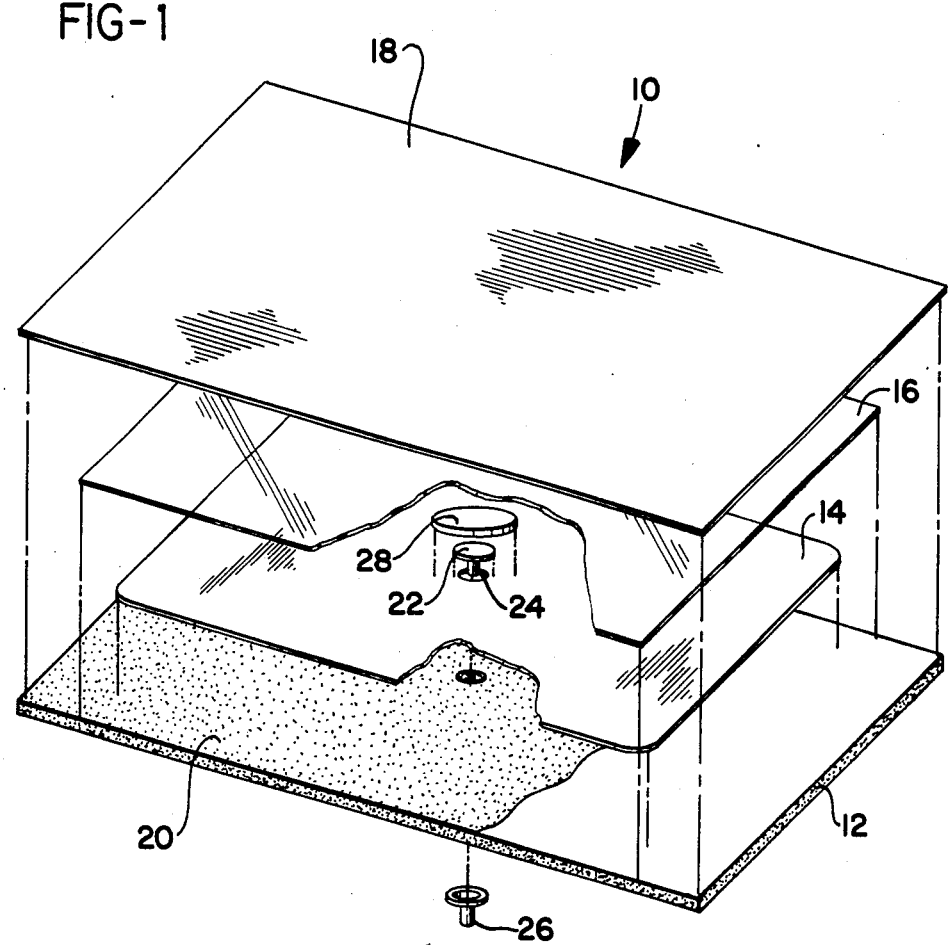
FIG. 1 is an exploded perspective view of one embodiment of the indifferent electrode of the present invention.
Figure 2:
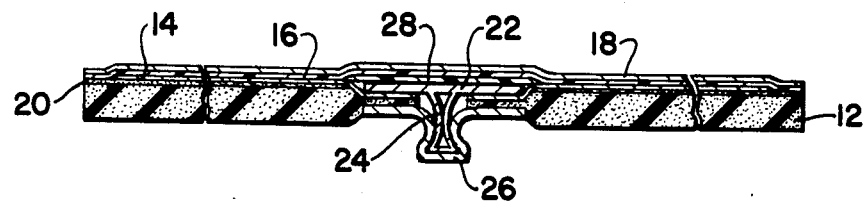
FIG. 2 is a sectional side view of an assembled indifferent electrode.

Referring to FIGS. 1 and 2, a capacitively coupled indifferent electrode 10 is shown. Although a rectangular configuration is illustrated, it has been found that the shape of the electrode is not important and can be a variety of shapes. The electrode includes a flexible, resilient backing material 12, a metal foil layer 14, a layer of dielectric material 16, and a protective cover sheet 18 having a release coating on the face thereof. Dielectric material 16 can be a film of a suitable nonconductive material coated with a pressure sensitive adhesive or, alternatively, a continuous film of a nonconductive pressure sensitive adhesive can serve as the dielectric layer. One surface of the backing material 12 is covered with a layer of a commercially available, medical grade acrylic pressure-sensitive adhesive 20. Metal foil layer 14 is then adhered to adhesive 20. The foil layer 14 and material 12 are then pierced by a metal rivet 22 having a shaft 24. Shaft 24 is of sufficient length to pass through both the metal foil layer 14 and backing material 12 and is mated with a metal socket 26 to provide an electrically conductive path through the pad. Socket 26 is then crimped to lock the shaft in place. Socket 26 can then be easily snap fitted to a return line of an electrosurgical generator. Alternatively, any suitable means to provide an electrically conductive path from foil layer 14 to the return side of an electrosurgical generator may be utilized.

A button 28 of an electrically nonconductive material such as nylon or other insulating material is interposed between rivet 22 and dielectric layer 16 to insure that the rivet will never come in direct contact with a patient's skin. Dielectric layer 16 may be of any suitable electrically nonconductive material which can be easily formed into a thin film such as polyethylene, polyvinyl chloride, polyethylene terephthalate, or polysulfone. Preferred dielectric materials are polyethylene terephthalate, available under the trademark Mylar from E. I. duPont de Nemours & Co. and polyvinylidene chloride available under the trademark Saran from Dow Chemical Co. These materials are flexible and strong and can be formed into films as little as 0.0005 inches thick. The dielectric layer 16 is coated on both sides with a suitable pressure-sensitive adhesive and is placed over metal foil layer 14. A 0.002 inch thickness of adhesive on both sides of the dielectric layer has been found to be suitable. Alternatively, a continuous film of pressure sensitive adhesive may serve as both the dielectric layer and adherence medium, and a separate layer of dielectric material is not required. It is important that the dielectric layer at least cover to the edges of the metal foil so that there is no exposed metal on the electrode. Although the electrode illustrated in FIGS. 1 and 2 has a backing material 12 with a surface area larger than metal foil layer 14, it is within the scope of the invention to provide dielectric and metal foil layers which extend to the edges of the backing pad. In this manner, the entire surface area of the apparatus is used.

Backing material 12 is preferably formed of a closed cell foamed plastic material such as polyurethane, polyvinyl chloride, or the like. Such materials will resist absorption of fluids. Alternatively, the backing material may be a fabric material. Such a sheet is quite flexible and readily conforms to skin contours. Foil 14 may be fabricated of any suitable electrically conductive material which can be made into a thin, flexible foil. Aluminum foil is preferred although it is also within the scope of this invention to use metallized plastic films such as a metallized polyethylene terephthalate film.

The invention may be better understood by reference to the following nonlimiting examples.

EXAMPLE I

Figure 3:
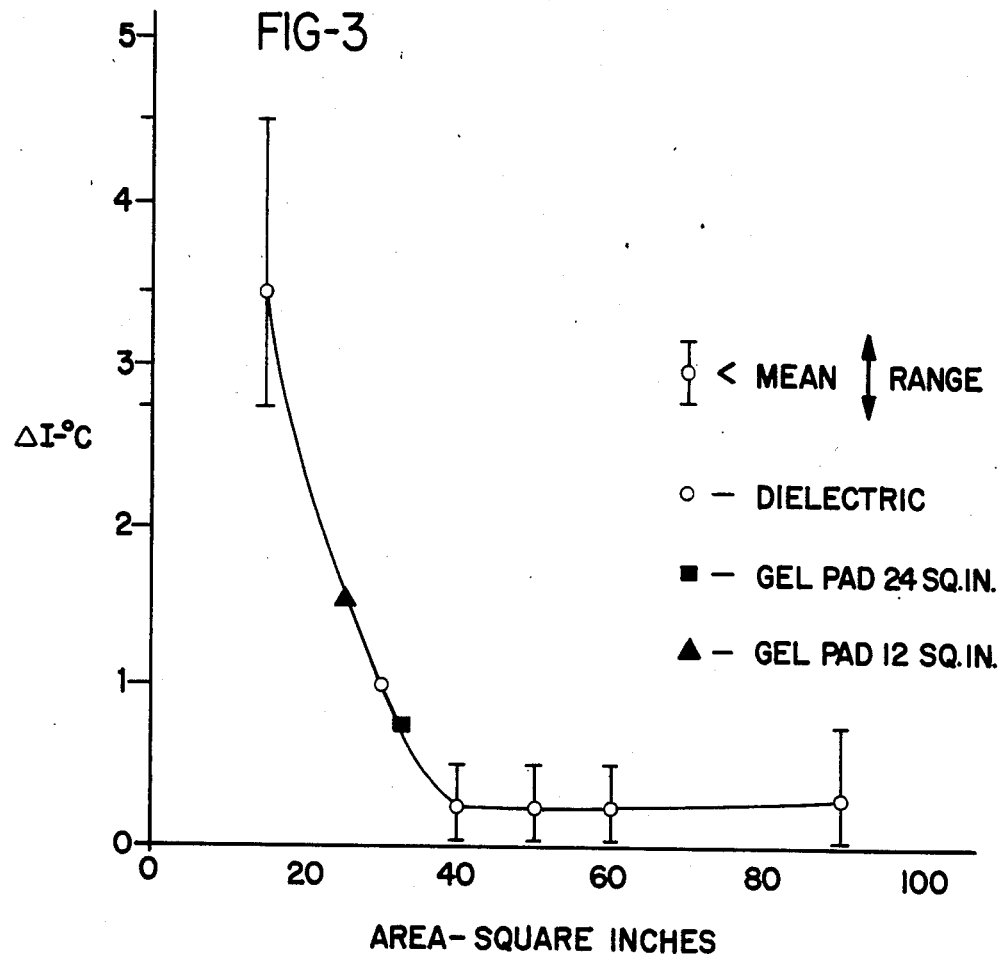
FIG. 3 is a graph of change in skin temperature versus surface area of the capacitively coupled indifferent electrode, with data points for two commercially available direct coupled indifferent electrodes being shown for comparison purposes.

Temperature measurements using a thermographic technique accurate to within 0.5° C. were carried out on human subjects to determine how varying the surface area of the indifferent electrode affected skin temperature at the point where the electrode was attached to the skin. A current of 1 amp was delivered to indifferent electrodes prepared in accordance with the teachings of the present invention attached to the abdominal area of a subject for a period of 1 minute. A 0.0005 inch thick film of Mylar was used as the dielectric material. These values of current flow and duration represent a "worst possible case" limit for delivered energy for electrosurgical procedures and were arrived at by analyzing the maximum likely values for over 80 surgical procedures. Thermograms were photographed approximately 30 seconds after the current was turned off. This represented the lowest feasible time in view of the necessity to remove the electrodes from the subject before a thermogram could be taken. The results of these tests are illustrated in FIG. 3. As can be seen, the greatest increase in skin temperature was for the 15 square inch electrode, with an exponential rise in heat occurring with decreasing electrode size below that point. At surface areas of 40 square inches and above, temperature increases amounted to about 0.5° C. with no apparent decrease in temperature with increased surface area electrodes. Normal skin temperature is approximately 31° C. while a temperature of approximately 45° C. is required before tissue damage occurs.

For comparison purposes, two commercially available pre-gelled, direct coupled indifferent electrodes were also tested. Their surface areas were 12 and 24 square inches, respectively. The temperature increases measured using those electrodes were placed on the data curve for the capacitively coupled electrode so that a comparison could be made. As shown in FIG. 3, an approximately 25 square inch capacitively coupled electrode would be required to result in an equivalent temperature increase as compared with a 12 square inch direct coupled electrode, and an approximately 33 square inch capacitively coupled electrode would be required to result in an equivalent temperature increase for a 24 square inch direct coupled electrode. Thus, by modestly increasing the surface area of the capacitively coupled electrode, its improved operational and safety characteristics can be used while maintaining essentially the same low skin temperature increase exhibited by commercially available direct coupled electrodes. Moreover, as shown by this worst case example, capacitively coupled electrodes of 30 square inches or larger cause a skin temperature increase far below the threshold for causing tissue damage.

EXAMPLE II

Figure 4:
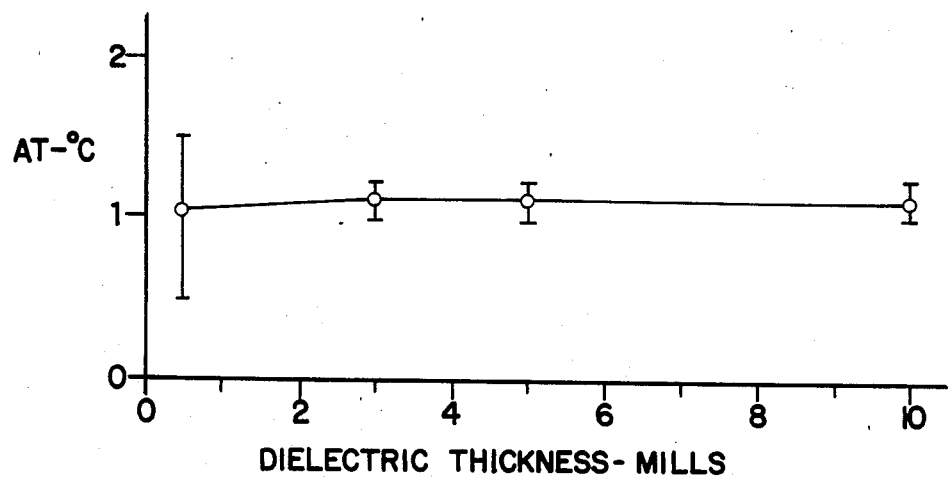
FIG. 4 is a graph of change in skin temperature versus dielectric thickness for a 30 square inch surface area capacitively coupled electrode.

Using a capacitively coupled electrode prepared in accordance with the practice of the present invention and having a skin contact surface area of 30 square inches, skin temperature increases were measured as in Example I for different thicknesses of dielectric material. Again, a 1 amp current was supplied for 60 seconds, and the dielectric material utilized was Mylar. As can be seen from FIG. 4, dielectric thickness is not critical in affecting increases in skin temperature. Dielectric material as little as 0.0005 inches thick produced as good results as material 20 times as thick. Therefore, some limiting factors in dielectric material thickness are the ability to produce a thin film and that film's physical properties to withstand the stresses of a manufacturing process. Of course, the thinness of the dielectric film is also limited by the breakdown voltage at which arcing across the dielectric will occur.

EXAMPLE III

The impedance (ratio of applied voltage to current) in a circuit using a capacitively coupled electrode was measured using electrodes with varying surface areas. Ideally, the impedance in a circuit should be low to avoid alternate path hazards. That is, if the resistance to current flow is large, the current applied at the active electrode may seek an alternate path to leave a patient's body other than through the return electrode. Thus, for example, if a patient were hooked up to an EKG monitor with small EKG electrodes, some of the current applied at the active electrosurgical electrode could seek to leave the patient's body at the site of an EKG electrode. Because of the small surface area of such electrodes, tissue damage at the site due to a heat buildup is a possibility.

Figure 5:
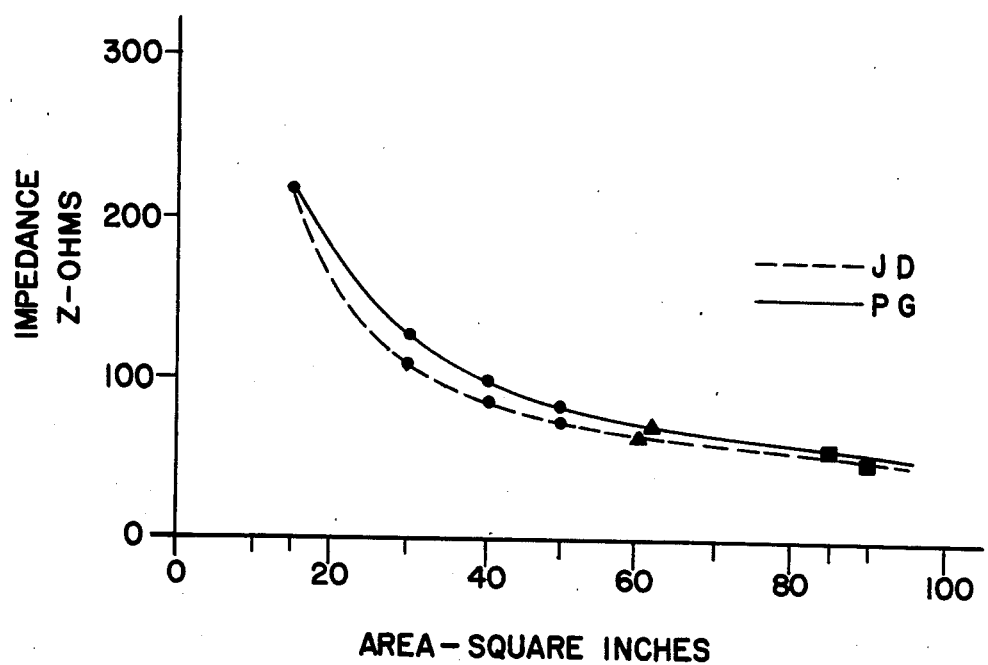
FIG. 5 is a graph of impedance versus surface area of the capacitively coupled electrode, with data points for two commercially available direct coupled indifferent electrodes being shown for comparison purposes.

As shown in FIG. 5, the impedance in a circuit decreases as the surface area of the capacitively coupled electrode increases. For the tests on two human test subjects (labeled JD and PG) a 1 amp current was applied at the active site, and the dielectric material used in the electrode was 0.0005 inch thick Mylar. The impedance of commercially available pre-gelled direct coupled electrodes was also measured and plotted on the impedance curve for comparison purposes. As in Example I, 12 and 24 square inch pre-gelled direct coupled electrodes were used.

Figure 6:
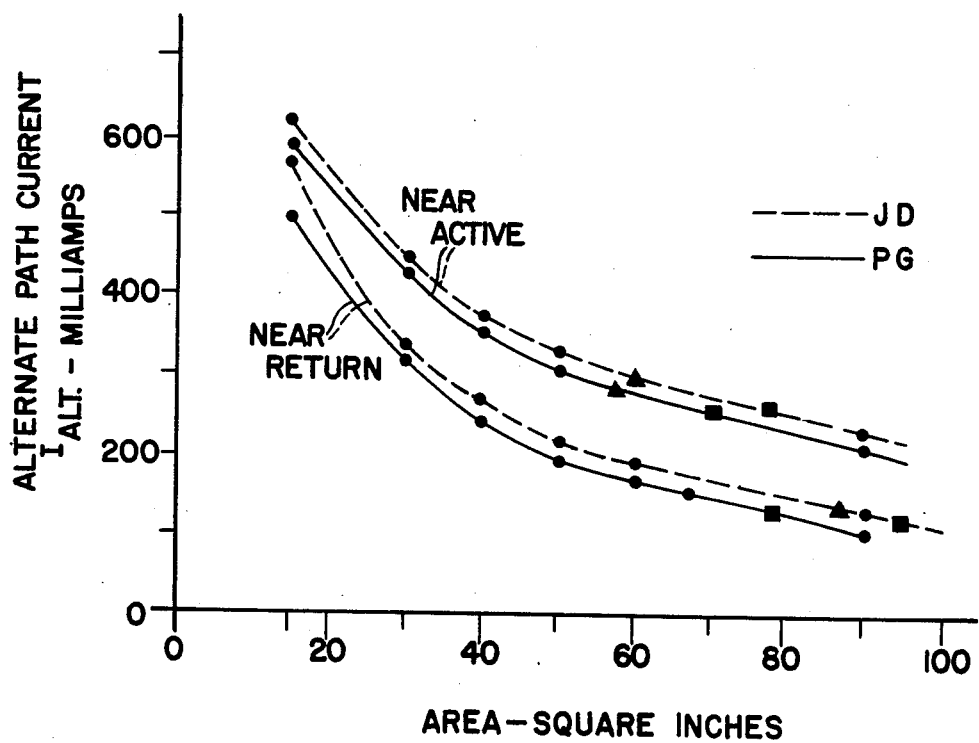
FIG. 6 is a graph of alternate path current versus surface area of the capacitively coupled electrode.

FIG. 6 illustrates the measured alternate path current for varying surface area sized capacitively coupled electrodes. A current normalized to 1 amp was applied at the active electrode site an a 0.0005 inch thick dielectric was used. Currents of less than 1 amp were used in some tests where the amount of alternate path current posed a heating problem with the small size EKG electrodes. All results reported have been normalized to a 1 amp current. Small EKG electrodes were positioned both near the active electrode site and near the capacitively coupled return electrode site. As can be seen, as the surface area of the capacitively coupled electrode increased, the alternate path current measured at the respective EKG electrodes decreased. This indicates that the larger the surface area of a capacitively coupled electrode, the less the alternate path hazard to a patient.

EXAMPLE IV

Figure 7:
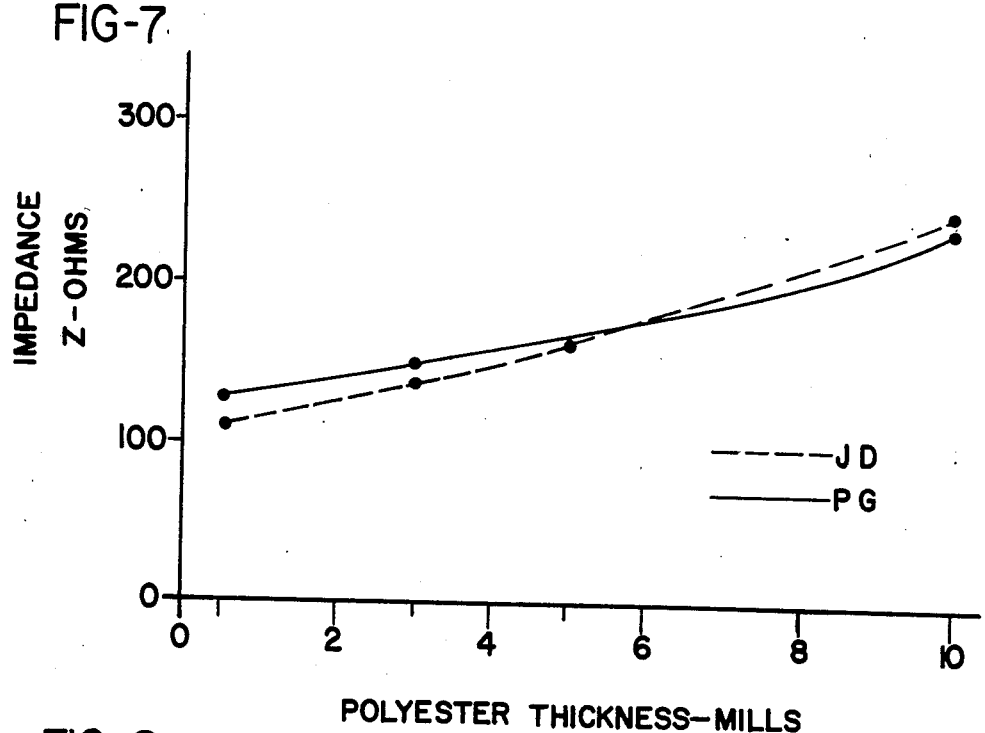
FIG. 7 is a graph of impedance versus dielectric thickness for a 30 square inch surface area capacitively coupled electrode.
Figure 8:
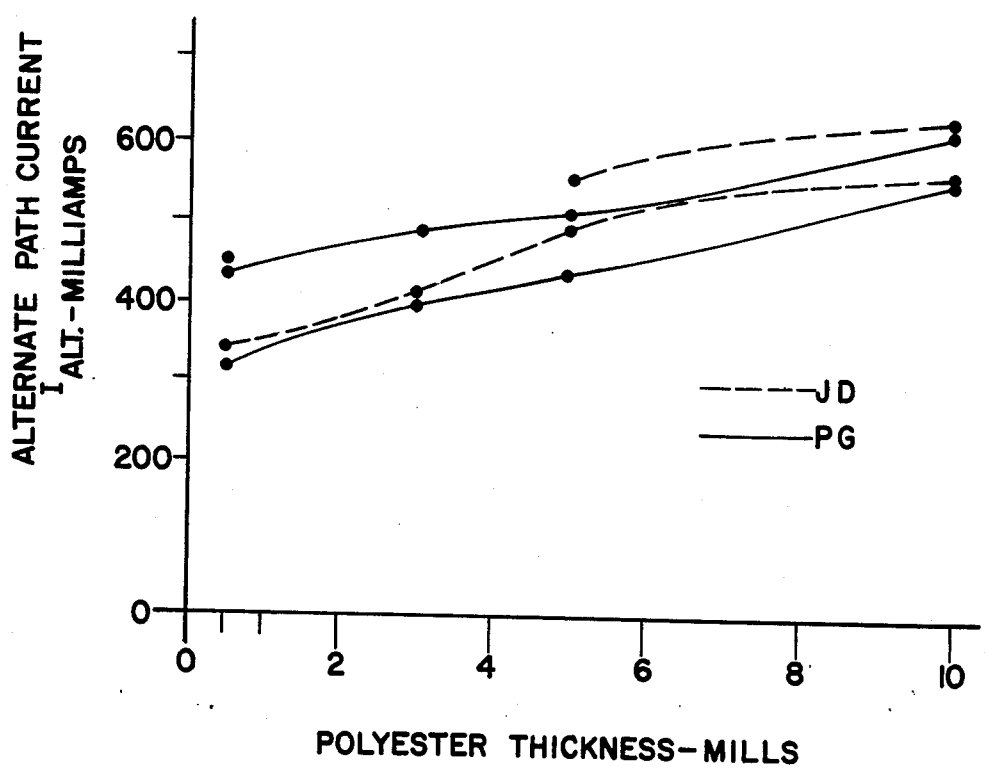
FIG. 8 is a graph of alternate path current versus dielectric thickness for a 30 square inch surface area capacitively coupled electrode.

FIGS. 7 and 8 compare impedances and alternate path currents for a fixed 30 square inch size capacitively coupled electrode with varying dielectric material thicknesses. Again, Mylar was used as the dielectric material and a current normalized to 1 amp as in Example III was applied at the active electrode site. As can be seen, both impedance and alternate path current increase with increasing dielectric thickness for both human tests subjects (labeled JD and PG).

The adhesive coated capacitively coupled electrode of the present invention provides both safe and reliable operation. Because the adhesive covers the entire surface of the electrode, it provides much more secure contact with a patient's skin and resists tenting or the formation of air gaps which could cause hot spots. Additionally, there is no requirement for a peripheral ring of adhesive around the edges of the electrode; the entire surface area can be utilized for an electrode surface. As shown by the examples, electrodes having surface areas of 30 square inches or more can be operated at high currents for up to 1 minute and still not create any dangerous rise in a patient's skin temperature. Because of the exponential heat rise with decreasing electrode size, a 15 square inch electrode appears to represent the practical limits for safe usage. However, even smaller size electrodes would have utility in controlled current applications.

While the apparatus described herein constitutes a preferred embodiment of the invention, it is to be understood that the invention is not limited to this precise apparatus, and that changes may be made without departing from the scope of the invention, which is defined in the appended claims.

What is claimed is:

1. A capacitively coupled indifferent electrode for use in electrosurgical procedures comprising:
   a flexible backing sheet;
   a thin, flexible electrically conductive foil mounted on said backing sheet;
   means for electrically connecting said electrically conductive foil to an electrosurgical current generator; and
   a layer of a dielectric material having a thickness between about 0.0005 and 0.001 inches mounted on and completely overlying said electrically conductive foil and forming a skin-contacting surface which is capable of capacitive coupling under electrosurgical conditions, the entire skin contacting surface of said dielectric material having a pressure-sensitive adhesive thereon to secure said indifferent electrode to a patient's skin.

2. The indifferent electrode of claim 1 in which said flexible sheet has a peripheral portion extending beyond the edges of said electrically conductive foil and said dielectric material, said peripheral portion having pressure-sensitive adhesive thereon to secure the electrode to a patient's skin.

3. The indifferent electrode of claim 1 in which said electrically conductive foil has a surface area of at least 15 square inches.

4. The indifferent electrode of claim 1 in which said dielectric material is selected from the group consisting of polyethylene, polyethylene terephthalate, polyvinylidene chloride, and polysulfone.

5. The indifferent electrode of claim 1 in which said dielectric material is adhered to said electrically conductive foil.

6. The indifferent electrode of claim 1 in which said electrically conductive foil is selected from the group consisting of aluminum and metallized polyethylene terephthalate.

7. The indifferent electrode of claim 1 in which said electrically conductive foil extends substantially completely to the edges of said flexible sheet.

8. The indifferent electrode of claim 7 in which said flexible sheet is fabricated of a polymeric foam material.

9. The indifferent electrode of claim 7 in which said flexible sheet is fabricated of a fabric material.

10. The indifferent electrode of claim 1 in which said electrical connecting means is a snap fastener.

11. In a capacitively coupled indifferent electrode for use in electrosurgical procedures including an electrically conductive foil, means for electrically connecting said electrically conductive foil to an electrosurgical generator, a layer of dielectric material overlying said electrically conductive foil and forming a skin-contacting surface, and a backing sheet supporting said electrically conductive foil and said dielectric material, the improvement comprising:

said dielectric material having a thickness of less than about 0.001 inches and equal to or greater than about 0.0005 inches and having a layer of pressure-sensitive adhesive completely covering said skin-contacting surface.

12. The indifferent electrode of claim 11 in which said electrically conductive foil extends substantially completely to the edges of said backing sheet.

13. The indifferent electrode of claim 11 in which said backing sheet has a peripheral portion extending beyond the edges of said dielectric material and said electrically conductive foil, said peripheral portion having a pressure-sensitive adhesive thereon for securing said electrode to a patient's skin.

14. A capacitively coupled indifferent electrode for use in electrosurgical procedures comprising a flexible backing sheet; a thin, flexible electrically conductive foil mounted on said backing sheet and defining a skin contacting surface; means for electrically connecting said electrically conductive foil to an electrosurgical current generator; and a layer of a dielectric material comprising a pressure sensitive adhesive mounted on and completely overlying said electrically conductive foil and forming a skin-contacting surface which is capable of capacitive coupling under electrosurgical conditions, said pressure sensitive adhesive covering the entire skin contacting surface of said electrically conductive foil to secure said indifferent electrode to a patient's skin.

* * * * *